(12) United States Patent
Lee et al.

(10) Patent No.: US 7,642,376 B2
(45) Date of Patent: Jan. 5, 2010

(54) METHODS AND DEVICES FOR PREPARING BIURET AND CYANURIC ACID

(75) Inventors: Chun Hyuk Lee, Siheung (KR); Min Seung Shin, Siheung (KR); Hoon Lee, Siheung (KR)

(73) Assignee: J & J Chemical Co. (KR)

( * ) Notice: Subject to any disclaimer, the term of this patent is extended or adjusted under 35 U.S.C. 154(b) by 314 days.

(21) Appl. No.: 11/837,242

(22) Filed: Aug. 10, 2007

(65) Prior Publication Data

US 2008/0039623 A1    Feb. 14, 2008

(30) Foreign Application Priority Data

Aug. 11, 2006   (KR) .................... 10-2006-0076212

(51) Int. Cl.
  *C07C 273/18*   (2006.01)
  *C07D 251/32*   (2006.01)

(52) U.S. Cl. ....................... 564/38; 544/192

(58) Field of Classification Search ............... 564/38; 544/192
  See application file for complete search history.

(56) References Cited

U.S. PATENT DOCUMENTS

| 1,324,277 A | 12/1919 | Schantz | 84/477 R |
| 3,057,918 A | 10/1962 | Formaini et al. | 564/38 |
| 3,928,438 A * | 12/1975 | Beale et al. | 564/38 |

FOREIGN PATENT DOCUMENTS

GB    1324277 A    7/1973

OTHER PUBLICATIONS

Russian Office Action and English Translation of Russian Office Action, Application No. 2007130685/04(033428), Oct. 27, 2008, 16 pages.
"Biuret and Related Compounds", Chemical Reviews, 56, pp. 95-197 (1956). 103 pages.

* cited by examiner

*Primary Examiner*—Peter G O'Sullivan
(74) *Attorney, Agent, or Firm*—St. Onge Steward Johnston & Reens LLC

(57) ABSTRACT

Provided are methods and devices for preparing biuret and cyanuric acid by thermal decomposition of urea. Specifically, a product of thermal decomposition is cooled to precipitate a crystal and the precipitated crystal is dissolved using an alkali aqueous solution and cooled to obtain biuret having high purity. Furthermore, the cyanuric acid that is one of byproducts by the thermal decomposition of urea is effectively recovered with high purity.

19 Claims, 1 Drawing Sheet

METHODS AND DEVICES FOR PREPARING BIURET AND CYANURIC ACID

CROSS-REFERENCE TO RELATED APPLICATIONS

The present application claims priority of Korean patent application No. 10-2006-0076212 filed on Aug. 11, 2006, the content of which is incorporated herein by reference.

FIELD OF THE INVENTION

The present invention relates to methods and devices for preparing biuret and cyanuric acid, and more particularly, to a method of preparing biuret having high purity in which products of thermal decomposition of urea like biuret, triuret, cyanuric acid are cooled to obtain a crystal, and the resultant crystal is dissolved using an alkali solution and cooled to obtain biuret having high purity, a device for preparing biuret, and a method and device for preparing cyanuric acid with high purity which is a byproduct of the thermal decomposition reaction of urea.

BACKGROUND OF THE INVENTION

In general, when urea is thermally decomposed at 130° C.-200° C., a condensation product including biuret is formed. Specifically, when the thermal decomposition is performed under reduced pressure, or ammonia that is a product of the thermal decomposition of urea is removed by passing air and nitrogen through a reactor, the thermal decomposition reaction is efficiently carried out so that biuret can be obtained in a great amount in a short period of time. In addition, as the thermal decomposition reaction is performed at high temperature, biuret can be formed quickly but more byproducts, such as a cyanuric acid, triuret, and melamine, may be formed ("Biuret and Related Compounds", Chemical Reviews, 56, pp. 95-197 (1956).)

A process of thermally decomposing urea to form biuret will now be described in detail.

Urea is heated to 130° C. or higher in a thermal decomposition reactor to form ammonia and a isocyanic acid as illustrated in Reaction Scheme 1:

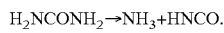  <Reaction Scheme 1>

Reaction Scheme 1 proceeds as urea absorbs heat. As the heating temperature is increased, urea is decomposed more quickly and isocyanic acid is formed more quickly. And as more ammonia is removed, more forward reaction occurs The isocyanic acid reacts with urea remaining in the reactor to form biuret according to Reaction Scheme 2:

  <Reaction Scheme 2>

The reaction of Reaction Scheme 2 is an exothermic reaction. As the temperature is increased, the isocyanic acid which exists in a great amount in an equilibrium state reacts with urea to form biuret. But at this time byproducts, such as a cyanuric acid and triuret are also formed Such processes for forming biuret have already been disclosed in many references which primarily focus on methods of recovering biuret in large amounts from the byproducts after biuret is formed.

U.S. Pat. No. 3,057,918 discloses a method of recovering biuret in which a crud biuret including a cyanuric acid and triuret is digested with 10% or more aqueous ammonia solution at 80° C.-110° C., and then cooled to obtain a crystal biuret having low solubility with respect to water. The US patent publication also discloses a method recovering a cyanuric acid having high purity by removing ammonia under reduced pressure from a solution from which biuret has been recovered The method described above, however, requires a separate complex device to maintain a concentration of the ammonia in the solution to a predetermined level when the digesting process is performed under pressure. In addition, the digesting process should be performed for a relatively long period of time, such as from 30 minutes to 2 hours. Furthermore, the cyanuric acid should be recovered under reduced pressure. That is, the method described above is expensive.

U.S. Pat. No. 1,324,277 discloses a method of forming biuret having high purity in which urea is dissolved in glycol ether and reacts at 110° C.-210° C. to obtain biuret having high purity. This method, however, includes a process of decomposing urea and a process of reducing the amount of residual urea to a level lower than a desired amount by decreasing the temperature, wherein the process of reducing the amount of residual urea should be performed for 2 to 6 hours. That is, this method also is expensive.

Accordingly, there is a need to develop an inexpensive method in which urea is thermally decomposed using a relatively simple method for a short period of time to obtain biuret having high purity.

SUMMARY OF THE INVENTION

The present invention provides a method of preparing biuret having high purity using a thermal decomposition reaction.

The present invention also provides a method of preparing cyanuric acid having high purity from a product of the thermal decomposition reaction.

The present invention also provides a device for preparing biuret having high purity using a thermal decomposition reaction The present invention also provides a device for preparing cyanuric acid having high purity from a product of the thermal decomposition reaction.

According to an aspect of the present invention, there is provided a method of preparing biuret, including: (a) melting urea; (b) performing a thermal decomposition reaction on the molten urea by heating; (c) adding water to the resultant thermal decomposition product to precipitate and filter a crude biuret crystal; (d) dissolving the crude biuret crystal using an alkali aqueous solution; (e) cooling the dissolved product to precipitate a biuret crystal; and (f) filtering the cooled product to obtain the biuret crystal and a mother liquor, and washing the biuret crystal.

According to another aspect of the present invention, there is provided method of preparing a cyanuric acid, the method including: (a) melting urea; (b) performing a thermal decomposition reaction on the molten urea by heating; (c) adding water to the resultant thermal decomposition product to precipitate and filter a crude biuret crystal; (d) dissolving the crude biuret crystal using an alkali aqueous solution; (e) cooling the dissolved product to precipitate a biuret crystal; (f) filtering the cooled product to obtain the biuret crystal and a mother liquor, and washing the biuret crystal; (g) neutralizing using an acid the filtered mother liquor obtained in (f) so as to precipitate a cyanuric acid crystal, thereby obtaining a cyanuric acid crystal-containing slurry; and (h) filtering and washing the cyanuric acid crystal-containing slurry to recover a cyanuric acid crystal.

According to another aspect of the present invention, there is provided device for preparing biuret, the device including: (1) a urea melter for melting urea; (2) a thermal decomposition reactor for thermally decomposing the molten urea by heating; (3) a first crystallizer for precipitating a crude crystal to obtain a crude crystal-containing slurry by adding water to the product generated in the thermal decomposition reactor and cooling the resultant solution; (4) a first filtering and washing device for obtaining a crude biuret crystal by filtering and washing the crude crystal-containing slurry; (5) a dissolving vessel for dissolving the crude biuret crystal using an alkali aqueous solution; (6) a second crystallizer for precipitating a purified biuret crystal to obtain a purified biuret crystal-containing slurry by cooling the dissolved product; and (7) a second filtering and washing device for filtering and washing the biuret crystal-containing slurry.

According to another aspect of the present invention, there is provided device for preparing a cyanuric acid, the device including: the device described above including: (1) a urea melter for melting urea; (2) a thermal decomposition reactor for thermally decomposing the molten urea by heating; (3) a first crystallizer for precipitating a crude crystal to obtain a crude crystal-containing slurry by adding water to the product generated in the thermal decomposition reactor and cooling the resultant solution; (4) a first filtering and washing device for obtaining a crude biuret crystal by filtering and washing the crude crystal-containing slurry; (5) a dissolving vessel for dissolving the crude biuret crystal using an alkali aqueous solution; (6) a second crystallizer for precipitating a purified biuret crystal to obtain a purified biuret crystal-containing slurry by cooling the dissolved product; and (7) a second filtering and washing device for filtering the purified biuret crystal-containing slurry to obtain a purified biuret crystal and a mother liquor and washing the purified biuret crystal; (8) a neutralizing device for neutralizing the mother liquor injected from the second filtering and washing device using an acid to precipitate a cyanuric acid crystal to obtain a cyanuric acid crystal-containing slurry; and (9) a third filtering and washing device for filtering and washing the cyanuric acid crystal-containing slurry to recover the cyanuric acid crystal.

In the case that biuret is prepared using a method and device for preparing biuret according to the present invention, a crude biuret crystal that is a thermal decomposition product can be dissolved using an alkali aqueous solution for a short period of time, and the resultant solution is cooled to selectively recover biuret having low solubility with respect to water at low temperature, and thus biuret having high purity can be obtained. In addition, after biuret is recovered, the mother liquor in which the purity of the cyanuric acid is high can be neutralized using an acid to form a crystal so as to obtain a cyanuric acid having high purity.

DETAILED DESCRIPTION OF THE INVENTION

Figure 1:
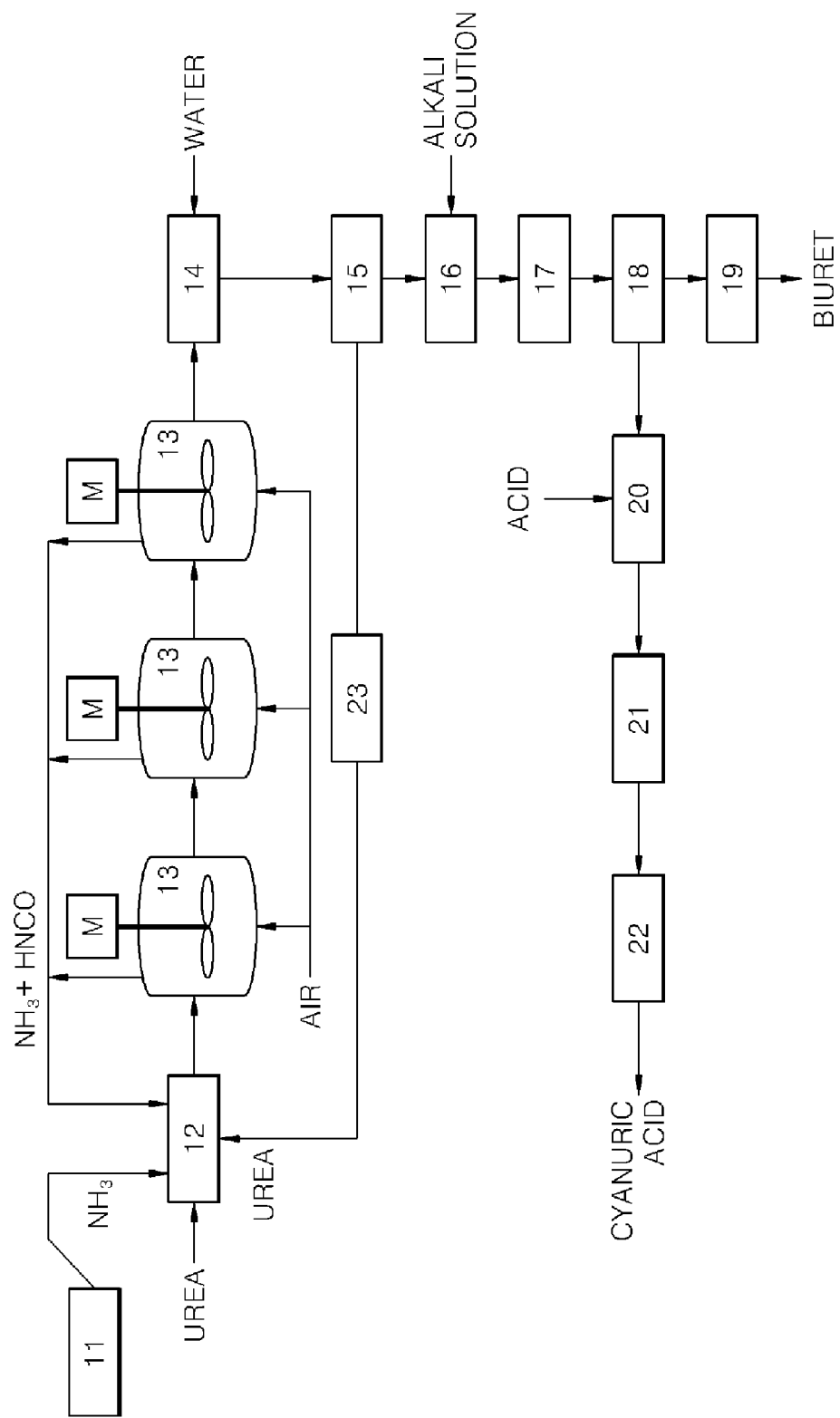
FIG. 1 is a schematic view of a system for preparing biuret in accordance with an embodiment of the present invention.

A method of preparing biuret according to an embodiment of the present invention includes: (a) melting urea; (b) performing a thermal decomposition reaction on the molten urea by heating; (c) adding water to the resultant product of the thermal decomposition to precipitate and filter a crude biuret crystal; (d) dissolving the crude biuret crystal using an alkali aqueous solution; (e) cooling the dissolved product to precipitate a biuret crystal; and (f) filtering the cooled product to obtain the biuret crystal and a mother liquor, and washing the biuret crystal.

In (a), the temperature of a urea melter 12 used to melt the urea therein may be in the range from 130° C. to 160° C., specifically, from 132° C. to 140° C. When the temperature of the urea melter 12 is less than 130° C., the urea may be incompletely melted. On the other hand, when the temperature of the urea melter 12 is more than 160° C., a self condensation reaction takes place and more byproducts are formed. After the urea is molten in the urea melter, the urea is injected to a thermal decomposition reactor 13 and heated.

In (b), the heating temperature may be in the range from 130° C. to 200° C., specifically, from 140° C. to 150° C. In such a temperature range, urea can react quickly and effectively with isocyanic acid. When the heating temperature is less than 130° C., non-molten urea may exist and the efficiency of a isocyanic acid formation reaction may be too low. On the other hand, when the heating temperature is more than 200° C., too many byproducts, such as a cyanuric acid, triuret, melamine, or amellide, in addition to biuret, may be formed.

The method may further include reloading the ammonia gas and isocyanic acid gas formed in (b) into (a). In (b), the thermal decomposition reaction may be performed by injecting air or inert gas through a lower portion of a reactor. When the air or inert gas is injected through a lower portion of a reactor, ammonia and unreacted isocyanic acid can exist in the air or inert gas ejected from the reactor and thus, the ammonia and unreacted isocyanic acid can be reinjected to the urea melter 12. In the urea melter 12, the reinjected isocyanic acid can react with urea to form biuret. Therefore, a conversion rate of urea due to the thermal decomposition reaction can be increased. The ammonia can be passed through a scrubber to be absorbed in water, and then transferred to a device for preparing a liquefied ammonia or an ammonia water having a predetermined concentration.

The thermal decomposition reaction can be performed in a single batch-type reactor or in a continuous-type reactor consisting of a plurality of reactors connected in series. To obtain efficiency and stability of the thermal decomposition reaction, a continuous-type reactor which is more efficient than the batch-type reactor may be used. When the number of the reactors is more than 7, a conversion rate increase effect cannot be further obtained, and thus, the economical efficiency may be decreased.

Products obtained as a result of the thermal decomposition reaction may include biuret, and byproducts, such as a cyanuric acid, triuret, or the like. In the present specification, the term 'a crude biuret' refers to a product including biuret and other such byproducts. The crude biuret is injected from the thermal decomposition reactor 13 to a first crystallizer 14, and then mixed with water and the resultant mixture is cooled to precipitate a crude biuret crystal to obtain a crude biuret crystal-containing slurry. The crude biuret crystal-containing slurry is filtered in a first filtering and washing device 15, and then injected to a dissolving vessel 16. The first filtering and washing device 15 may use a centrifuge or a vacuum filtering device.

In (c), the mother liquor may primarily include urea, and the urea is transferred to a water evaporating device 23 and heated at reduced pressure to evaporate water. The resultant urea is reinjected to the urea melter 12 to manufacture biuret.

The crystal filtered in the first filtering and washing device 15, that is, the crude biuret crystal, can be dissolved in an alkali aqueous solution. The alkali aqueous solution may be an aqueous solution of a hydroxide of an alkali metal or an aqueous solution of a hydroxide of an alkaline earth meta, specifically, an aqueous solution of NaOH, KOH, or $Ca(OH)_2$. The alkali aqueous solution may have a concentration in the range from about 10% to 50%. The alkali aqueous solution dissolves biuret, cyanuric acid, and triuret to obtain a solution, and specifically, reacts with the cyanuric acid to form a salt to significantly increase the solubility of the cyanuric acid. Accordingly, the alkali aqueous solution which is added to react with the cyanuric acid to form a salt should be used in a suitable equivalent ratio with respect to the cyanuric acid. According to the present invention, the amount of the alkali solution may be in the range from 0.5 to 5 mole that is equivalent to 1 mole of the cyanuric acid in the crude biuret crystal. When the amount of the alkali aqueous solution used is too small, less cyanuric acid salt is formed and thus, in the cooling process, biuret having high purity cannot be obtained. On the other hand, when the amount of the alkali aqueous solution used is too large, the concentration of biuret is too low and biuret may not be precipitated in the subsequent cooling process.

In (d), the alkali aqueous solution may be added in a suitable temperature range to obtain dissolving efficiency and stability. According to the present invention, the dissolving temperature may be in the range from 50° C. to 105° C., specifically, in the range from 60° C. to 80° C. When the dissolving temperature is lower than 50° C., the dissolving time of the crude biuret crystal with respect to the alkali aqueous solution may be too long and thus the economical efficiency may be decreased. On the other hand, when the dissolving temperature is higher than 105° C., biuret may decompose and thus the yield thereof may be reduced.

The solution obtained using the alkali aqueous solution in (d) is cooled. The cooling process can be performed using a cooling coil-type, a plate-type, or a shell & tube-type heat exchange device. In the current embodiment, the cooling process may be performed at a temperature of 5° C. to 40° C. When the cooling temperature is less than 5° C., the crude biuret solution may become so sticky that may have some trouble in processing. On the other hand, when the cooling temperature is higher than 40° C., only small amount of biuret can be obtained because of increasing solubility of biuret. In the cooling process, biuret having low solubility with respect to water may be precipitated in the form of crystals but the cyanuric acid which exists in a salt may dissolve completely.

The resultant slurry including the biuret crystal is filtered and washed in a second filtering and washing device 18 to recover a biuret crystal. The recovered biuret crystal is dried to obtain the biuret crystal having high purity which is the objective of the present invention.

A method of preparing a cyanuric acid according to an embodiment of the present invention includes: (a) melting urea; (b) performing a thermal decomposition reaction on the molten urea by heating; (c) adding water to the resultant product of the thermal decomposition to precipitate and filter a crude biuret crystal; (d) dissolving the crude biuret crystal using an alkali aqueous solution; (e) cooling the dissolved product to precipitate a biuret crystal; (f) filtering the cooled product to obtain the biuret crystal and a mother liquor, and washing the biuret crystal; (g) neutralizing the mother liquor obtained from (f) using an acid so as to precipitate a cyanuric acid crystal, thereby obtaining a cyanuric acid crystal-containing slurry; and (h) filtering and washing the cyanuric acid crystal-containing slurry to recover a cyanuric acid crystal.

Accordingly, the method of preparing a cyanuric acid according to the current embodiment includes the same processes as in the method according to the previous embodiment, that is specifically includes performing a thermal decomposition reaction on the molten urea by heating; adding water to the resultant product of the thermal decomposition to precipitate a crude biuret crystal and filtering the crude biuret crystal; dissolving the crude biuret crystal using an alkali aqueous solution; cooling the dissolved product to precipitate a biuret crystal; and filtering the biuret crystal;

In (g), the cyanuric acid salt is neutralized using an acid. In the current embodiment, the acid can be an inorganic acid, such as a hydrochloric acid, a sulfuric acid, a nitric acid, or a phosphoric acid; or an organic acid, such as an acetic acid, a carboxylic acid, a formic acid, an oxalic acid, or a benzoic acid. Furthermore, the acid can be any acid having a pH of less than 7.

The crystal precipitated by neutralizing the mother liquor with an acid in (g) has a large amount of the cyanuric acid. The crystal-containing slurry is filtered and water-washed in a third filtering and washing device 20 to obtain a cyanuric acid having high purity.

A device for preparing biuret according to an embodiment of the present invention includes:

(1) a urea melter for melting urea;

(2) a thermal decomposition reactor for thermally decomposing the molten urea by heating;

(3) a first crystallizer for precipitating a crude crystal to obtain a crude crystal-containing slurry by adding water to the product generated in the thermal decomposition reactor and cooling the resultant product;

(4) a first filtering and washing device for obtaining a crude biuret crystal by filtering and washing the crude crystal-containing slurry;

(5) a dissolving vessel for dissolving the crude biuret crystal using an alkali aqueous solution;

(6) a second crystallizer for precipitating a purified biuret crystal to obtain a purified biuret crystal-containing slurry by cooling the dissolved product; and (7) a second filtering and washing device for filtering the purified biuret crystal-containing slurry to obtain a purified biuret crystal and a mother liquor and washing the purified biuret crystal.

The ammonia scrubber 11, the urea melter 12, the thermal decomposition reactor 13, the first and second crystallizers 14 and 17, the first and second filtering and washing devices 15 and 18, and the alkali dissolving vessel 16 are already described above.

The device according to the current embodiment may further include a device capturing the ammonia gas and isocyanic acid gas generated in the thermal decomposition reactor 13 and re-loading the captured gases to the urea melter 12. By including such a re-loading device, loss of the unreacted isocyanic acid gas can be minimized, and thus, a conversion rate from urea to biuret can be increased. Meanwhile, ammonia generated as a result of the thermal decomposition reaction is passed through a scrubber 11 so that the generated ammonia is absorbed to the scrubber 11, and then, injected to a device of preparing a liquefied ammonia or an ammonia water having a predetermined concentration and thus can be used in a separate processes.

The thermal decomposition reactor 13 can be a single batch-type reactor or a continuous-type reactor consisting of a plurality of reactors connected in series. To obtain efficiency and stability of the thermal decomposition reaction, a continuous-type reactor which is more efficient than the batch-type reactor may be used. When the number of the reactors is more than 7, a conversion rate increase effect cannot be further obtained, and thus, the economical efficiency may be decreased.

The device according to the current embodiment may further include a device in which water in the mother liquor obtained in the first filtering and washing device of (4) is evaporated and the resultant solution is transferred to the urea melter of (1). The mother liquor obtained in the first filtering and washing device of (4) according to the current embodiment primarily includes urea. The mother liquor is injected to a water evaporating device 23 and then heated under reduced pressure to evaporate water. The resultant urea is transferred to the urea melter 12 to rejoin the thermal decomposition reaction. Therefore, urea can be reused and the manufacturing costs may be reduced.

The alkali aqueous solution added to the dissolving vessel 16 of (5) according to the current embodiment can be an aqueous solution of a hydroxide of an alkali metal or an aqueous solution of a hydroxide of an alkaline earth metal, specifically, an aqueous solution of NaOH, KOH, or $Ca(OH)_2$. The alkali aqueous solution may have a concentration in the range from about 10% to 50%. A loading device of the alkali aqueous solution is not limited. For example, the alkali aqueous solution can be injected through an outer load line, or the alkali aqueous solution can be directly injected to an alkali aqueous solution vessel.

In the current embodiment, the temperature of the dissolving vessel 16 of (5) may be in the range from 50° C. to 105° C., specifically, from 60° C. to 80° C. When the temperature of the dissolving vessel 16 of (5) is lower than 50° C., the dissolving time of the crude biuret crystal in the alkali solution is too long such that the economical efficiency may be decreased. On the other hand, when the temperature of the dissolving vessel 16 of (5) is higher than 105° C., biuret may decompose.

The biuret obtained using the device for preparing biuret according to the current embodiment does not include a cyanuric acid, such that the biuret has high purity. In addition, the biuret can be obtained using a simple device so that the manufacturing costs may be reduced.

A device for preparing a cyanuric acid according to another embodiment of the present invention includes: (1) a urea melter for melting urea; (2) a thermal decomposition reactor for thermally decomposing the molten urea by heating; (3) a first crystallizer for precipitating a crude crystal to obtain a crude crystal-containing slurry by adding water to the product generated in the thermal decomposition reactor and cooling the resultant product; (4) a first filtering and washing device for obtaining a crude biuret crystal by filtering and washing the crude crystal-containing slurry; (5) a dissolving vessel for dissolving the crude biuret crystal using an alkali aqueous solution; (6) a second crystallizer for precipitating a purified biuret crystal to obtain a purified biuret crystal-containing slurry by cooling the dissolved product; (7) a second filtering and washing device for filtering the purified biuret crystal-containing slurry to obtain a purified biuret crystal and a mother liquor and washing the purified biuret crystal; (8) a neutralizing device for neutralizing the mother liquor injected from the second filtering and washing device using an acid to precipitate a cyanuric acid crystal to obtain a cyanuric acid crystal-containing slurry; and (9) a third filtering and washing device for filtering and washing the cyanuric acid crystal-containing slurry to recover the cyanuric acid crystal.

In (8), the acid used to neutralize the mother liquor can be an inorganic acid, such as a hydrochloric acid, a sulfuric acid, a nitric acid, or a phosphoric acid; or an organic acid, such as an acetic acid, a carboxylic acid, a formic acid, an oxalic acid, or a benzoic acid. Furthermore, the acid can be any acid having a pH of less than 7.

The neutralizing device 19, and the third filtering and washing device 20 which filters the cyanuric acid crystal are already described Up to this point, the method and device for preparing biuret and the method and device for preparing a cyanuric acid have been described.

In the case of the methods and devices according to the present invention, a crude biuret crystal is dissolved using an alkali aqueous solution and then cooled to obtain a biuret crystal. Therefore, the biuret having higher purity and a cyanuric acid having higher purity can be more easily produced in a shorter period of time than when an ammonia digesting technique is used.

The present invention will be described in further detail with reference to the following examples. These examples are for illustrative purposes only and are not intended to limit the scope of the present invention.

EXAMPLES

Example 1

Urea (produced by SigmaAldrich Co.) was dissolved in a urea melter at 140° C., and then injected to a thermal decomposition reactor at a predetermined loading rate. The temperature of the thermal decomposition reactor was maintained at 160° C. The thermal decomposition reactor was a continuous-type reactor consisting of three reactors connected in series. The air was injected to the thermal decomposition reactor through a lower portion of the thermal decomposition reactor in an amount of 1 mole of air per 1 mole of urea. Therefore, when the air passed out from the thermal decomposition reactor, the air included ammonia and unreacted isocyanic acid. The resultant air was transferred to the urea melter so that the unreacted isocyanic acid reacted with urea. The product obtained from thermal decomposition reactor was continuously injected to a cooling tank to precipitate a crude biuret crystal. At this time, the average residual time of the product in the cooling tank was controlled to be about 150 minutes. The product obtained from the thermal decomposition reactor was recovered to measure a conversion rate of urea. As a result, the conversion rate of urea was about 35%. The product of the thermal decomposition reaction was identified using liquid chromatography. Based on 100 parts by weight of urea injected, the amount of biuret was 29.8 parts by weight, the amount of urea was 50.9 parts by weight, the amount of cyanuric acid was 3.0 parts by weight, and the amount of triuret was 1.3 parts by weight. That is, the total weight of biuret, urea, cyanuric acid, and triuret was 85 parts by weight. The 100 parts by weight of urea injected minus the total weight of the generated product was 15 parts by weight, and such loss was caused since the unreacted isocyanic acid and the ammonia escaped from the thermal decomposition reactor. Hereinafter, the amount of each component was measured in a unit of parts by weight based on 100 parts by weight of urea injected.

85 parts by weight of water was injected to 85 parts by weight of the thermal decomposition product and cooled to 15° C. while mixing, and then the reaction product was centrifugally dehydrated. A dehydrated cake containing crystal was washed with 15 parts by weight of water to remove the remaining urea. As a result, the amount of the cake obtained was 28 parts by weight. The cake excluding water was identified using a liquid chromatography. As such, the amount of biuret was 85.7 wt %, the amount of urea was 1.8 wt %, the amount of cyanuric acid was 8.9 wt %, and the amount of triuret was 3.6 wt %. In addition, the mother liquor obtained by dehydrating was identified using liquid chromatography. As a result, the amount of biuret was 4.1 wt %, the amount of urea was 35.5 wt %, the amount of cyanuric acid was 0.3 wt %, the amount of triuret was 0.2 wt % and the amount of water was 59.9 wt %. The mother liquor obtained by dehydrating was heated at a temperature of 110 to 130° C. under a pressure of 200 mmHg and then reinjected to the urea melter. The composition of the resultant solution right before being reinjected to the urea melter was identified. As a result, the amount of biuret was 12.2 wt %, the amount of urea was 86.5 wt %, the amount of cyanuric acid was 0.9 wt %, and the amount of triuret was 0.4 wt %. Then, urea was additionally injected to the urea melter. Through such processes, in the composition of a thermal decomposition product of the thermal decomposition reactor, a conversion rate of biuret was increased to reach an equilibrium state. In the equilibrium state, the composition of the thermal decomposition product included 37.3 wt % of biuret, 57 wt % of urea, 4.2 wt % of the cyanuric acid, and 1.5 wt % of triuret.

72 parts by weight of water was further added to a dehydrated crude biuret cake, and then 2.5 mole that is equivalent to 1 mole of NaOH aqueous solution with respect to the mole of the cyanuric acid was added thereto and heated at 70° C. for 20 minutes to decompose all of the thermal decomposition product. At this time, the cyanuric acid reacted with the NaOH aqueous solution to form a cyanuric acid salt which is very soluble in water. The resultant solution prepared by dissolving with the NaOH aqueous solution was injected to a cooling tank and cooled to 10° C. At this time, biuret was crystallized and precipitated. The resultant solution was dehydrated using a centrifuge, and washed with water to obtain a purified biuret. As a result, as high as 99.5 weight percent biuret was obtained.

Furthermore, the dehydrated mother liquor was injected to a neutralizing tank and then HCL was added thereto until the pH of the solution in the neutralizing tank was decreased to 4. At this time, a cyanuric acid was precipitated. The resultant solution was dehydrated at 50° C. and washed with water to obtain a purified cyanuric acid. At this time, as high as 99 weight percent cyanuric acid was obtained.

Comparative Example 1

122 parts by weight of water, and 28.6 parts by weight of ammonia (19% ammonia water) were added to 85 parts by weight of a crude biuret cake obtained through thermal decomposing, cooling, and filtering processes according to Example 1 and then mixed together. The resultant solution was heated to a temperature of 90° C. to 100° C. and left to sit for 30 minutes, and then, cooled to 50° C. and the pressure in the reactor used was gradually reduced was reduced to atmospheric pressure to precipitate a biuret crystal. At this time, a cyanuric acid was combined with ammonia and as such became soluble with respect water. Therefore, the cyanuric acid was not precipitated. The resultant slurry was filtered and the mother liquor cake was washed with water and dried. The dried product was identified using liquid chromatography. As a result, the amount of biuret was 98%, the amount of urea was 0.5%, the amount of the cyanuric acid was 0.3%, and the amount of triuret was 1.2%.

In methods and devices according to the present invention, a crude biuret crystal generated by thermally decomposing urea is dissolved using an alkali aqueous solution. Accordingly, compared to a conventional method, the methods of preparing biuret having high purity and cyanuric acid having high purity according to the present invention are simple and inexpensive. Meanwhile, unreacted isocyanic acid obtained in a thermal decomposition process is transferred to a urea melter. In addition, urea obtained by dehydrating a mother liquor of a thermal decomposition product is transferred to a urea melter. Therefore, the loss of urea can be reduced and a conversion rate of the urea can be increased, which is very economical. Furthermore, ammonia generated in the processes is absorbed using a scrubber and the absorbed ammonia can be re-used in a separate process.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of preparing biuret, comprising steps:
   (a) melting urea;
   (b) performing a thermal decomposition reaction on the molten urea by heating;
   (c) adding water to the resultant product of the thermal decomposition to precipitate and filter a crude biuret crystal;
   (d) dissolving the crude biuret crystal using an alkali aqueous solution;
   (e) cooling the dissolved product to precipitate a biuret crystal; and
   (f) filtering the cooled product to obtain the biuret crystal and a mother liquor, and washing the biuret crystal.

2. The method of claim 1, wherein in step (a), the urea is heated in a melter at a temperature from 130° C. to 160° C.

3. The method of claim 1, wherein in step (b), the heating temperature is in the range from 130° C. to 200° C.

4. The method of claim 1, wherein an ammonia gas and a iso-cyanic acid gas are generated in step (b), and the generated ammonia gas and isocyanic acid gas are transferred to step (a).

5. The method of claim 1, wherein step (b) is performed by loading air or inert gas to a lower portion of a reactor.

6. The method of claim 1, wherein step (b) is performed using a batch-type reactor, or a continuous-type reactor comprising a plurality of reactors connected in series.

7. The method of claim 1, wherein a mother liquor obtained from step (c) is dehydrated and then transferred to step (a).

8. The method of claim 1, wherein in step (d), the alkali aqueous solution is an aqueous solution of a hydroxide of an alkali metal or an aqueous solution of a hydroxide of an alkaline earth metal.

9. The method of claim 1, wherein in step (d), the amount of the alkali aqueous solution injected is in the range from 0.5 to 5 mole that is equivalent to 1 mole of a cyanuric acid contained in the crude biuret crystal.

10. The method of claim 1, wherein in step (d), the alkali aqueous solution is used at a temperature of 50° C. to 105° C.

11. The method of claim 1, wherein in step (e), the dissolved product is cooled to a temperature ranging from 5° C. to 40° C.

12. A method of preparing a cyanuric acid, the method comprising steps:
   (a) melting urea;
   (b) performing a thermal decomposition reaction on the molten urea by heating;
   (c) adding water to the resultant product of the thermal decomposition to precipitate and filter a crude biuret crystal;
   (d) dissolving the crude biuret crystal using an alkali aqueous solution;
   (e) cooling the dissolved product to precipitate a biuret crystal;

(f) filtering the cooled product to obtain the biuret crystal and a mother liquor, and washing the biuret crystal;

(g) neutralizing, using an acid, the filtered mother liquor so as to precipitate a cyanuric acid crystal, thereby obtaining a cyanuric acid crystal-containing slurry; and (h) filtering and washing the cyanuric acid crystal-containing slurry to recover a cyanuric acid crystal.

13. The method of claim 12, wherein the acid is an organic acid or an inorganic acid.

14. A device for preparing biuret, the device comprising:
a urea melter for melting urea;
a thermal decomposition reactor for thermally decomposing the molten urea by heating;
a first crystallizer for precipitating a crude crystal to obtain a crude crystal-containing slurry by adding water to the product generated in the thermal decomposition reactor and cooling the resultant solution;
a first filtering and washing device for obtaining a crude biuret crystal by filtering and washing the crude crystal-containing slurry;
a dissolving vessel for dissolving the crude biuret crystal using an alkali aqueous solution;
a second crystallizer for precipitating a purified biuret crystal to obtain a purified biuret crystal-containing slurry by cooling the dissolved product; and
a second filtering and washing device for filtering the purified biuret crystal-containing slurry to obtain a purified biuret crystal and a mother liquor and washing the purified biuret crystal.

15. The device of claim 14, further comprising a device for capturing ammonia gas and isocyanic acid gas which are generated in the thermal decomposition reactor to re-load the ammonia gas and isocyanic acid gas to the urea melter.

16. The device of claim 14, wherein the thermal decomposition reactor is a batch-type reactor or a continuous-type reactor comprising a plurality of reactors connected in series.

17. The device of claim 14, further comprising a device for dehydrating a mother liquor obtained in the first filtering and washing device to re-load to the urea melter.

18. The device of claim 14, wherein the alkali aqueous solution is an aqueous solution of a hydroxide of an alkali metal or an aqueous solution of a hydroxide of an alkaline earth metal.

19. A device for preparing a cyanuric acid, the device comprising:
a urea melter for melting urea;
a thermal decomposition reactor for thermally decomposing the molten urea by heating;
a first crystallizer for precipitating a crude crystal to obtain a crude crystal-containing slurry by adding water to the product generated in the thermal decomposition reactor and cooling the resultant solution;
a first filtering and washing device for obtaining a crude biuret crystal by filtering and washing the crude crystal-containing slurry;
a dissolving vessel for dissolving the crude biuret crystal using an alkali aqueous solution;
a second crystallizer for precipitating a purified biuret crystal to obtain a purified biuret crystal-containing slurry by cooling the dissolved product;
a second filtering and washing device for filtering the purified biuret crystal-containing slurry to obtain a purified biuret crystal and a mother liquor and washing the purified biuret crystal
a neutralizing device for neutralizing the mother liquor injected from the second filtering and washing device using an acid to precipitate a cyanuric acid crystal to obtain a cyanuric acid crystal-containing slurry; and
a third filtering and washing device for filtering and washing the cyanuric acid crystal-containing slurry to recover the cyanuric acid crystal.

* * * * *